United States Patent [19]

Costantini et al.

[11] 4,208,536

[45] Jun. 17, 1980

[54] HYDROXYLATION OF AROMATIC COMPOUNDS

[75] Inventors: Michel Costantini, Lyons; Adrien Dromard, Paris; Michel Jouffret, Francheville le Bas; Roland Nantermet, Lyons, all of France

[73] Assignee: Rhone-Poulenc Industries, Paris, France

[21] Appl. No.: 752,903

[22] Filed: Dec. 21, 1976

[30] Foreign Application Priority Data

Dec. 24, 1975 [FR] France .................... 75 40382

[51] Int. Cl.² .................... C07C 37/00; C07C 39/08
[52] U.S. Cl. .................... 568/771; 568/800
[58] Field of Search .............. 260/621 G, 621 R, 625; 568/771, 800

[56] References Cited

U.S. PATENT DOCUMENTS

| | | | |
|---|---|---|---|
| 2,440,233 | 4/1948 | Krieble et al. | 260/621 G |
| 3,839,467 | 10/1974 | Vesely | 260/619 R |
| 3,849,502 | 11/1974 | Bourdin et al. | 260/621 G |
| 3,850,995 | 11/1974 | Horlenkv et al. | 260/621 G |
| 3,872,156 | 3/1975 | Bourdin et al. | 260/621 G |

*Primary Examiner*—Werren B. Lone
*Attorney, Agent, or Firm*—Burns, Doane, Swecker & Mathis

[57] ABSTRACT

Aromatic compounds of the general formula

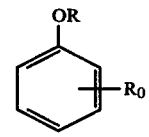

in which R and $R_o$ represents a hydrogen atom or an alkyl radical of 1 to 4 carbon atoms are hydroxylated by reaction with hydrogen peroxide in the presence of a catalytic amount of a strong acid and the reaction is carried out in the presence of an activator which is a juxtanuclear aromatic aldehyde or derivative thereof selected from an acetal or a benzhydrol.

20 Claims, No Drawings

HYDROXYLATION OF AROMATIC COMPOUNDS

BACKGROUND OF THE INVENTION

1. Field of the Invention

The present invention relates to a process for hydroxylating aromatic compounds and more particularly a process for hydroxylating phenols and phenol ethers by means of hydrogen peroxide.

2. Description of the Prior Art

Numerous processes for the oxidation of phenols and phenol ethers by means of hydrogen peroxide together with metal salts, or by means of organic per-acids (formed from hydrogen peroxide and a carboxylic acid) have been described. Depending on the particular case, these processes have made it possible to introduce a hydroxyl group into the nucleus of the aromatic compound or have resulted in a more or less extensive oxidation of this nucleus, ranging from the production of quinones to the opening of the benzene ring, with the formation of degradation products[cf. A. CHWALA et al. J. Prakt. chem. 152 46 (1939); G. G. HENDERSON et al., J. Chem. Soc. 91 1659–69 (1910); S. L. FRIESS et al., J. Am. Chem. Soc. 74 1305 (1952); H. FERNHOLZ, Chem. Ber. 87 578 (1954); H. DAVIDGE et al., J. Chem. Soc. 1958 4569; J. D. McCLURE et al., J. Org. Chem. 27 627-8 (1962)]. None of these processes is of industrial value, either because the yields of hydroxylation products are poor or because the reaction conditions are unsuitable for industrial exploitation or because the oxidizing agent is inconvenient or even dangerous to employ.

U.S. Pat. No. 3,514,490 has proposed carrying out the hydroxylation of phenol by means of per-acids (performic acid) in the presence of phosphoric acid. Although this process represents an advance relative to those described before, it remains necessary to use relatively large amounts of carboxylic acids, which play a part in requiring an increase in the volume of the apparatus; the same is true of all the processes which employ the carboxylic per-acids, such as those described in French Pat. No. 2,146,195 and in Belgian Pat. No. 809,204. For this reason, attempts have been made to dispense with the use of per-acids and to employ hydrogen peroxide directly as the hydroxylating agent. Thus, U.S. Pat. No. 3,407,237 has proposed hydroxylating aromatic compounds by means of hydrogen peroxide in the presence of hydrofluoric acid; in fact, the hydrofluoric acid acts as the reaction medium, so that this process cannot be put into operation industrially.

Ultimately, none of the above-mentioned processes has made it possible industrially to carry out the hydroxylation of aromatic compounds by means of hydrogen peroxide and especially the hydroxylation of phenol to give hydroquinone and pyrocatechol. U.S. Pat. No. 3,849,502 has proposed a process for hydroxylating aromatic compounds, and more particularly phenol and its ethers, by means of hydrogen peroxide, alone, the characteristic feature of which resides in the fact that the reaction is carried out in the presence of a strong acid used in catalytic amount and, if appropriate, in the presence of a complexing agent for transition metals, such as ortho-, pyro- or poly-phosphoric acids or their esters, the initial water content, by weight, of the reaction mixture being less than 20% of the mixture of aromatic compound, water and hydrogen peroxide. This process represents a solution of the problem of hydroxylation of aromatic compounds, especially of phenol, on an industrial scale by virtue of its simplicity (in practice it requires only the use of catalytic amounts of strong acids [for example, perchloric acid, sulphuric acid or sulphonic acid, and of metal complexing agents (pyrophosphoric acid)] and because of the excellent yields of hydroxylation products which it provides. However, the achievement of these yields also depends on the degree of conversion of the aromatic compounds, which must be less than 30%, the value being controlled by an appropriate choice of the molar ratio of hydrogen peroxide to phenol. Preferably, the degree of conversion is restricted to a value of at most 15% and in practice values of 4 to 10% are not exceeded. Under these conditions, a limitation in the productivity of the apparatus results, because the process requires that the conversion of the aromatic compound should only be very limited and, separating off the hydroxylation products, a large volume of starting reactants should be recycled. It is thus important to ensure that the reaction should take place at as high a rate as possible so as to limit, to the maximum degree, the residence time of the reactants in the apparatus.

For given conditions of temperature and for a given water content of the medium, the rate of reaction depends on the nature of the acid, and for a given acid, on the amount of acid present in the reaction mixture. Regardless of the acid used, it appears desirable to be able to increase the rate of reaction without increasing the amount of acid and, preferably, even with a decrease in this amount. In practice, the acid used as the catalyst is extracted from the reaction mixture by washing with water, the wash waters being discarded as effluents after treatment, so that the acid catalyst is not recovered. It is thus important, from an industrial point of view, to be able to increase the productivity of the apparatus by increasing the rate of the reaction without increasing the required amount of catalyst and even with a reduction in this amount.

SUMMARY OF THE INVENTION

The present invention relates to an improvement of the process described in U.S. Pat. No. 3,849,502, which improvement makes it possible to increase the rate of the reaction without having to increase the amount of catalyst present or to raise the reaction temperature.

More particularly, the present invention relates to a process for hydroxylating aromatic compounds of the general formula

in which R and $R_o$, which may be the same or different, represent a hydrogen atom or an alkyl radical containing from 1 to 4 carbon atoms, by means of hydrogen peroxide, in the presence of a catalytic amount of a strong acid, and if appropriate in the presence of a complexing agent for metal ions, the water content, by weight, of the reaction medium being less than 20% of the mixture of aromatic compound, $H_2O_2$ and water, the said process being characterized in that the reaction is carried out in the presence of juxtanuclear aromatic aldehydes or of their derivatives selected from the group consisting of their acetals and the benzhydrols.

DETAILED DESCRIPTION OF THE INVENTION

Although any juxtanuclear aromatic aldehyde or any acetal or any benzhydrol derived from such an aldehyde can be used in the process according to the invention, it is preferred to employ the aldehydes, acetals and benzhydrols having the following general formulae:

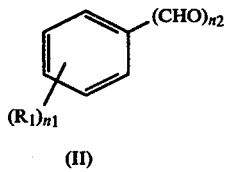 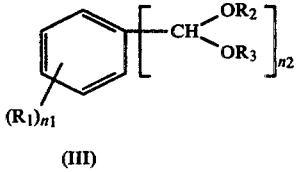 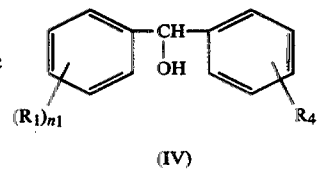

(II)     (III)     (IV)

in which:
$n_1$ is 0, 1, 2 or 3,
$n_2$ is 1 or 2,
$R_1$ represents a hydroxyl group, an alkoxy group having from 1 to 4 carbon atoms, a linear or branched alkyl radical having from 1 to 4 carbon atoms, or a halogen atom (if $n_1$ is greater than 1 the various $R_1$ radicals can be the same or different), or, finally, one of the radicals $R_1$ can represent a divalent group of the formula

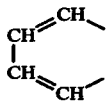

which is optionally substituted by a hydroxyl group, a halogen atom or an alkyl or alkoxy radical such as those defined above, this divalent radical forming a new aromatic ring with two carbon atoms, in the ortho-position, of the benzene ring,
$R_2$ and $R_3$, which may be the same or different, represent alkyl radicals such as those defined for $R_1$, and
$R_4$ represents a hydrogen atom, a hydroxyl group, an alkoxy radical or an alkyl radical having from 1 to 4 carbon atoms, the alkoxy or alkyl radicals being linear or branched.

More specifically;
$R_1$ represents a chlorine or bromine atom, or a methyl, ethyl, propyl, isopropyl, butyl, isobutyl, methoxy, ethoxy, propoxy or butoxy radical,
$R_2$ and $R_3$ represent a methyl, ethyl, propyl or isobutyl radical and
$R_4$ represents a methyl or ethyl radical.

In the formulae (II) to (IV), the various symbols $n_1$, $n_2$, $R_1$, $R_2$, $R_3$ and $R_4$ preferably represent the following:
$n_1$: 0, 1 or 2.
$n_2$: 1.
$R_1$: a hydroxyl group, a chlorine or bromine atom or a methoxy, ethoxy, methyl or ethyl radical.
$R_2$ and $R_3$ (preferably the same): a methyl or ethyl radical.
$R_4$: a hydroxyl group or a methoxy, ethoxy, methyl or ethyl radical.

As specific examples of aromatic aldehydes which can be used in the process of the invention, there may be mentioned: benzaldehyde, ortho-tolualdehyde, meta-tolualdehyde, p-tolualdehyde, 2,3-dimethyl-benzaldehyde, 2,5-dimethyl-benzaldehyde, 2-ethyl-benzaldehyde, 3-ethyl-benzaldehyde, 3-isopropyl-benzaldehyde, salicylaldehyde, 3-hydroxy-benzaldehyde, 3-iso-propoxy-benzaldehyde, 2-chloro-benzaldehyde, 3-chloro-benzaldehyde, 4-chloro-benzaldehyde, 3-bromo-benzaldehyde, isophthalaldehyde, phthalaldehyde, terephthalaldehyde, 4-hydroxy-2-methyl-benzaldehyde, 4-methoxy-2-methyl-benzaldehyde, 4-ethoxy, 2-methyl-benzaldehyde, 6-hydroxy-2-methyl-benzaldehyde, 2-hydroxy, 3-methyl-benzaldehyde, 4-methoxy-3-benzaldehyde, 4-ethoxy-3-methyl-benzaldehyde, 4-hydroxy-2,6-dimethyl-benzaldehyde and α-naphthaldehyde.

As non-limiting examples of acetals which can be employed, there may be mentioned the dimethyl- and diethyl-acetals of benzaldehyde, of ortho-tolualdehyde, of meta-tolualdehyde, of para-tolualdehyde, of 3,5-dimethyl-benzaldehyde, of anisaldehyde, of 2-ethoxy-benzaldehyde and of 3-chloro-benzaldehyde.

Amongst the benzhydrols which can be used for carrying out the process according to the invention there may be mentioned benzhydrol, 4-hydroxy-benzhydrol, 2-methoxy-4'-hydroxy-benzhydrol, 4-methoxy-benzhydrol, 4-ethoxy-benzhydrol, 3-ethoxy-benzhydrol, 2,3'-dihydroxy-benzhydrol, 2,4'-dihydrol, 4-hydroxy-4'-methyl-benzhydrol and 4-hydroxy-3'-methyl-benzhydrol.

In the text which follows, the aromatic aldehydes and the compounds derived therefrom will, for reasons of convenience, be referred to as the "activator".

In the case of phenol, it has also been noted that amongst the activators of the formula (II) to (IV), some exert an effect both on the rate of the reaction and on the selectivity with regard to the formation of the hydroquinone, by increasing the production of this compound at the expense of the pyrocatechol. Thus, certain of the above-mentioned activators make it possible to increase the molar ratio of hydroquinone/pyrocatechol from a value less than 1 to a value greater than 1. Hence, this provides a simple means of varying the production of these two products in accordance with requirements. Amongst the compounds which exert such an effect there may be mentioned benzaldehyde, p-chloro-benzaldehyde, benzhydrol and 4-hydroxy-benzhydrol.

These compounds are used preferentially if it is desired to improve both the rate of reaction and its selectivity with respect to the formation of hydroquinone.

The increase in the rate of the reaction depends, all other things being equal, on the nature of the compounds of the formula (II), (III) or (IV) which are used as activators and, for a given compound, on the amount employed; hence, this provides a flexible means of regulating the rate of the reaction to the desired value. The amount of activator will thus be decided in accordance with its nature and with the chosen residence time. In general, amounts of at least $1 \times 10^{-4}$ mol per mol of hydrogen peroxide are used, and amounts of between $1 \times 10^{-4}$ mol and 1 mol of activator per mol of hydrogen peroxide are very suitable. However, it is not necessary to exceed 0.5 mol of activator per mol of $H_2O_2$;

in practice, the amount of activator is most frequently between 0.01 and 0.5 mol per mol of $H_2O_2$.

The general conditions for carrying out the process according to the invention are those of the process described in U.S. Pat. No. 3,849,502, of which the present invention is an improvement. Thus, the amount of hydrogen peroxide employed is preferably less than 0.3 mol per mol of aromatic compound and more preferred less than 0.15 mol per mol of aromatic compound. The concentration of the aqueous hydrogen peroxide solution, though in itself not critical, is chosen so as to introduce as little water as possible into the reaction medium. In general, an aqueous hydrogen peroxide solution containing at least 20% by weight of $H_2O_2$ is used.

The strong acids used in the present process are, in accordance with definition of the acids given in U.S. Pat. No. 3,849,502, those of which the pK in water at ambient temperature is below $-0.1$ and preferably below $-1$. Amongst the acids which correspond to this definition, it is preferred to use those which are stable to hydrogen peroxide under the reaction conditions. The halogenated or non-halogenated inorganic oxy-acids such as sulphuric, chloro-sulphonic, perchloric and nitric acid, and the sulphonic acids are particularly suitable. Amongst the latter there may be mentioned methanesulphonic, trifluoromethanesulphonic, ethanesulphonic, ethanedisulphonic, methoxysulphonic, benzenesulphonic, benzenedisulphonic, toluenesulphonic, naphthalenesulphonic and naphthalenedisulphonic acid and the sulphonated polymers such as those derived from styrene. The amount of acid, which may be expressed by the ratio of the number of equivalents of protons to the number of mols of hydrogen peroxide can vary within wide limits; for example, the ratio $H^+/H_2O_2$ can vary between $1\times10^{-4}$ and 1 and preferably between $1\times10^{-3}$ and 0.5.

As agents for complexing the transition metal ions which are stable towards hydrogen peroxide under the reaction conditions, it is possible to employ, in particular, the various phosphoric and polyphosphoric acids such as orthophosphoric and pyrophosphoric or their ester-acids, for example the monoalkyl or dialkyl orthophosphates, the monocycloalkyl or dicycloalkyl orthophosphates, and the monoalkylaryl or dialkylaryl orthophosphates (ethyl or diethyl phosphate, hexyl phosphate, cyclohexyl phosphate and benzyl phosphate).

The amount of complexing agent depends on the content of metal ions in the reaction mixture. An amount which represents from 0.0001 to 5% of the mixture. An amount which represents from 0.0001 to 5% of the mixture by weight is generally very suitable.

The temperature at which the process can be carried out can vary between 20° and 150° C.

The reaction can be carried out in the presence of solvents which are stable towards hydrogen peroxide such as the aliphatic or cycloaliphatic hydrocarbons or their halogenated derivatives (chloroform and dichloroethane), and nitrated aromatic hydrocarbons such as nitrobenzene or nitrotoluene, particularly if the chosen reaction temperature is below the melting point of the aromatic compound.

Amongst the aromatic compounds which can be hydroxylated by the process of the invention there may be mentioned phenol, anisole, phenetole and cresol.

The process according to the invention is particularly simple to carry out, whether continuously or in a batch operation. At the end of the reaction, the unconverted aromatic compound and, where appropriate, the activator, are separated from the hydroxylation products by conventional means, especially by distillation, and are returned to the reaction zone. This process is particularly suitable for the hydroxylation of phenol. Although the effect of the aromatic aldehydes and of their derivatives on the rate of the reaction manifests itself regardless of the way in which the reactants are introduced, it has been found that this effect is still more significant if the acid catalyst is added to the mixture of the aromatic compound, the activator and the hydrogen peroxide.

The following examples are set forth as illustrating the invention, but not as limiting the same:

EXAMPLE 1

94 g of molten phenol containing 1,100 parts per million of water, 0.791 g of phosphoric acid of 85% concentration by weight, 0.985 g of benzaldehyde and 1.008 g of perchloric acid of 70% concentration by weight are charged into a 3-neck 250 cm$^3$ flask, equipped with a thermometer, a stirring device, a reflux condenser, a heating system and a nitrogen inlet, after flushing the flask with nitrogen.

The contents of the flask are kept at 45° C. and 2.028 g of hydrogen peroxide of a concentration of 84.7% by weight are then added. The disappearance of the active oxygen is followed by iodometric determinations on test samples kept at the temperature of an acetone/solid carbon dioxide mixture. After 1 minute under these conditions, 50% of the active oxygen has been converted. The reaction is complete in 44 minutes. The reaction mixture is neutralized by adding a N/2 potassium hydroxide solution in methanol and is then diluted by adding an equal volume of methanol. The reaction products are then determined by gas-liquid chromatography; the following results were obtained:

hydroquinone: 2.57 g
pyrocatechol: 1.98 g

The yields of hydroquinone and pyrocatechol respectively amount to 46.4 and 35.6% relative to the hydrogen peroxide employed. The ratio of the hydroquinone formed to the pyrocatechol is 1.3.

By way of comparison, the preceding experiment was repeated, but in the absence of benzaldehyde. Under these conditions, it required 19 minutes to achieve the disappearance of 50% of the active oxygen and 3 hours 12 minutes to achieve its complete conversion; the yields of hydroquinone and pyrocatechol relative to the hydrogen peroxide employed are respectively 33.7% and 52.3%; the hydroquinone/pyrocatechol ratio is 0.64.

Comparison of all this experiment with the preceding experiment shows the influence of the benzaldehyde on the rate of the reaction and on the ratio of the products formed.

EXAMPLES 2 to 9

Following the procedure described in Example 1, various experiments were carried out, varying the nature of the activator, the reaction conditions being as follows:

temperature 45° C.;
phenol containing 1,100 parts per million of water: 1 mol;
$H_3PO_4$ of a weight concentration of 85% in sufficient amount to introduce 0.05% by weight of acid into the reaction mixture;
$H_2O_2$ of a weight concentration of 71%: 0.0975 g (0.00065 mol);

activator: 0.011 mol.

The molar ratios of the reactants are as follows:
phenol/H$_2$O$_2$=20
HClO$_4$/H$_2$O$_2$=0.0127
activator/H$_2$O$_2$=0.22

For practical reasons and to insure that the various experiments should be comparable, the disappearance of the active oxygen was followd by iodometry until 50% of the active oxygen had decomposed. This time is referred to hereafter as the "reaction half-life" and is represented by "t ½" in the table which follows. The influence of the activators tested is accordingly illustrated by the time which must elapse to achieve disappearance of 50% of the hydrogen peroxide. Nevertheless, the yields of diphenols relative to H$_2$O$_2$ employed were determined as in Example 1 at the end of the reaction. The results obtained are shown in the following table:

TABLE I

| Example No. | Activator | t ½ in minutes | YIELDS/H$_2$O$_2$ hydroquinone (HQ) % | pyrocatechol (PC) % | HQ/PC |
|---|---|---|---|---|---|
| Comparative experiment | nil | 88 | 30.4 | 45.85 | 0.66 |
| 2 | benzaldehyde | 24 | 40.6 | 37 | 1.09 |
| 3 | m-tolualdehyde | 12 | 33.8 | 44.2 | 0.76 |
| 5 | o-tolualdehyde | 1 | 22.4 | 42 | 0.53 |
| 6 | p-chlorobenzaldehyde | 19 | 40.3 | 33 | 1.2 |
| 7 | p-hydroxybenzaldehyde | <1 | 33.2 | 54.5 | 0.6 |
| 8 | benzhydrol | 8 | 38.3 | 33.8 | 1.13 |
| 9 | 4-hydroxy-benzhydrol | 5 | 51.5 | 25.5 | 2 |

EXAMPLES 10 to 12

The procedure followed is as in the preceding examples, but the phosphoric acid and the perchloric acid are added to the other reactants, kept at a suitable temperature, and the temperature is varied, the amount of activator remaining constant; the amounts of reactants were as follows:

| | |
|---|---|
| phenol | 94 g |
| benzaldehyde | 1.06 g |
| 70% strength HClO$_4$ | 0.0975 g |
| 85% strength H$_3$PO$_4$ | 0.084 g |
| 84.7% strength H$_2$O$_2$ | 2.02 g |

The results are shown in the following table:

TABLE II

| Example No. | Temperature in C. | t ½ in minutes | YIELD HQ | PC | HQ/PC |
|---|---|---|---|---|---|
| 10 | 45 | 7 | 43.2 | 33 | 1.3 |
| 11 | 75 | 4 | 33.7 | 47.6 | 0.7 |
| 12 | 90 | 1 | 32.4 | 44.3 | 0.73 |

EXAMPLES 13 to 15

Following the procedure of Examples 10 to 12, a series of experiments was carried out, varying the molar ratio of benzaldehyde/H$_2$O$_2$. The reactants introduced and other conditions were as follows:

| | |
|---|---|
| temperature | 45° C. |
| 70% strength HClO$_4$ | 0.0975 g |
| 85% strength H$_3$PO$_4$ | 0.09 g |
| 84.7% strength H$_2$O$_2$ | 2.03 g |

The results are shown in the following table:

TABLE III

| Example No. | benzaldehyde in g | benzaldehyde H$_2$O$_2$ | t ½ in minutes | YIELDS HQ% | PC% | HQ/PC |
|---|---|---|---|---|---|---|
| 13 | 0.275 | 0.05 | 14 | 38.7 | 43.7 | 0.88 |
| 14 | 1.09 | 0.2 | 7 | 43.2 | 33 | 1.3 |
| 15 | 2.65 | 0.5 | 5 | 38.3 | 27.3 | 1.4 |

These experiments were carried out using the same batch of phenol as in Examples 10 to 12.

EXAMPLE 16

The procedure of Examples 10 to 12 was followed, with the following amounts of reactants:

| | |
|---|---|
| phenol | 94 g |
| benzaldehyde | 1.091 g |
| 70% strength HClO$_4$ | 0.706 g |
| 85% strength H$_3$PO$_4$ | 0.067 g |
| 84.7% strength H$_2$O$_2$ | 2.107 g |

In order to be able to carry out the hydroxylation at 25 C, the reaction is carried out in the presence of 0.33 mol of nitrobenzene as the solvent. Under these conditions, the following results were obtained:

| | |
|---|---|
| t ½ | 9 minutes |
| Yields | of hydroquinone: 40.4% |
| | of pyrocatechol: 25.1% |
| ratio HQ/PC | 1.6 |

We claim:
1. In a process for hydroxylating an aromatic compound of the general formula:

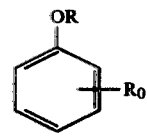

in which R and R$_o$, which may be the same or different, represent a hydrogen atom or an alkyl radical of from 1 to 4 carbon atoms, wherein said aromatic compound is reacted in the liquid phase at 20° to 150° C. with hydrogen peroxide in an amount such that the molecular ratio of hydrogen peroxide to the aromatic compound is less than 0.3 in the presence of a catalytic amount of a strong acid having a pK H$_2$O value below −0.1 and which is stable to oxidation by hydrogen peroxide, the amounts of hydrogen peroxide and strong acid being such that the ratio of the amount of acid, expressed in proton equivalents, to the number of molecules of hydrogen peroxide taking part in the reaction is at least equal to $1\times 10^{-4}$, the water content, by weight, of the reaction medium being less than 20% of the mixture of aromatic compound, hydrogen peroxide and water, and wherein the reaction is carried out in the presence of an agent which complexes transition metal ions and is stable under the reaction conditions, the improvement which consists of carrying out the reaction in the presence of an activator which is a juxtanuclear aromatic aldehyde or a derivative thereof selected from the group consisting of an acetal and a benzyhydrol.

2. A process according to claim 1, wherein said activator is an aldehyde of the general formula:

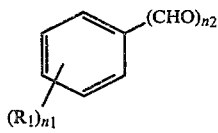

in which
$n_1$ is 0, 1, 2 or 3,
$n_2$ is 1 or 2, and
$R_1$ represents a hydroxyl group, an alkoxy group of from 1 to 4 carbon atoms, a linear or branched alkyl radical of from 1 to 4 carbon atoms, a halogen atom, or a divalent grouping of the formula:

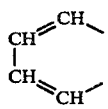

attached is adjacent carbon atoms of the benzene ring or such a grouping substituted by a hydroxy group, a halogen atom or an alkyl or alkoxy radical of from 1 to 4 carbon atoms, the radicals $R_1$ being the same or different when $n_1$ is 2 or 3.

3. A process according to claim 2, wherein $R_1$ represents a methoxy, ethoxy, methyl or ethyl radical, or a chlorine or bromine atom, $n_1$ is 0, 1 or 2 and $n_2$ is 1.

4. A process according to claim 3, wherein the activator is benzaldehyde, salicylaldehyde, p-hydroxybenzaldehyde, o-tolualdehyde, m-tolualdehyde or p-chlorobenzaldehyde.

5. A process according to claim 1, wherein the activator is an acetal of the general formula:

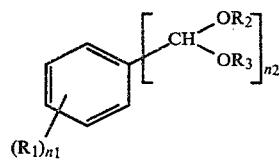

in which $R_1$, $n_1$ and $n_2$ have the meanings given in claim 2, and $R_2$ and $R_3$, which may be the same or different, represent linear or branched alkyl radicals of from 1 to 4 carbon atoms.

6. A process according to claim 5, wherein $R_1$ represents a hydroxyl group, a chlorine atom or a methoxy, ethoxy, methyl or ethyl radical, $R_2$ and $R_3$ are the same and represent methyl or ethyl radicals, $n_1$ is 0, 1, or 2 and $n_2$ is 1.

7. A process according to claim 1, wherein the activator is a benzhydrol of the general formula:

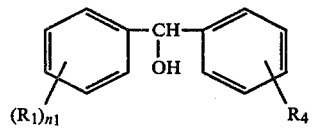

in which $R_1$ and $n_1$ have the meanings given in claim 2 and $R_4$ represents a hydrogen atom, a hydroxyl group or an alkoxy or alkyl radical of from 1 to 4 carbon atoms.

8. A process according to claim 7, wherein the activator is benzhydrol or 4-hydroxy-benzhydrol.

9. A process according to claim 1, wherein the amount of activator present is at least $1\times 10^{-4}$ mol per mol of hydrogen peroxide.

10. A process according to claim 9, wherein the amount of activator present is between $1\times 10^{-4}$ and 1 mol/mol of hydrogen peroxide.

11. A process according to claim 1, wherein the strong acid is an acid having a pK in water, at normal temperature, below $-1$.

12. A process according to claim 11, wherein the strong acid is a halogenated or non-halogenated inorganic oxy-acid.

13. A process according to claim 12, wherein the strong acid is sulphuric acid, chlorosulphonic acid or perchloric acid.

14. A process according to claim 11, wherein the strong acid is methanesulphonic acid, trifluoromethanesulphonic acid, benzenesulphonic acid, toluenesulphonic acid or a sulphonated resin.

15. A process according to claim 1, wherein the amount of strong acid present is such that the ratio $H^+/H_2O_2$ is at least equal to $1\times 10^{-3}$.

16. A process according to claim 1, wherein said agent is a phosphoric acid or its ester-acid.

17. A process according to claim 1, wherein said ratio is less than 0.15.

18. A process according to claim 1, wherein the aromatic compound is phenol.

19. A process according to claim 1, wherein the aromatic compound is phenol and the hydroxylated product is selected from the group consisting of hydroquinone, pyrocatechol and mixtures thereof.

20. A process according to claim 19, wherein hydroquinone is formed as the predominant reaction product.

* * * * *